United States Patent [19]
Sunberg et al.

[11] 4,446,052
[45] May 1, 1984

[54] AQUEOUS GEL CONTAINING TRICALCIUM DI(1-HYDROXY-3-AMINOPROPANE-1,1-DIPHOSPHONATE

[75] Inventors: Richard J. Sunberg, Oxford; James J. Benedict, Cincinnati, both of Ohio

[73] Assignee: The Procter & Gamble Company, Cincinnati, Ohio

[21] Appl. No.: 379,234

[22] Filed: May 17, 1982

[51] Int. Cl.$^3$ .............................................. B01J 13/00
[52] U.S. Cl. ...................... 252/315.1; 252/DIG. 11; 424/19; 424/54; 424/204; 424/DIG. 6
[58] Field of Search .................... 252/315.1, DIG. 11; 260/502.5 R, 502.5 E

[56] References Cited

U.S. PATENT DOCUMENTS

| | | |
|---|---|---|
| 3,101,301 | 8/1963 | Siegal et al. ................ 252/315.1 X |
| 3,608,067 | 9/1971 | Irani . |
| 3,683,080 | 8/1972 | Francis . |
| 3,962,432 | 6/1976 | Schmidt-Dunker . |
| 4,054,598 | 10/1977 | Blum et al. . |
| 4,200,539 | 4/1980 | Burnham et al. ............ 252/315.1 X |
| 4,327,039 | 4/1982 | Blum et al. ................... 260/502.5 C |

OTHER PUBLICATIONS

P. Gysen and G. Heynen, *Anal. Chem. Symp. Ser.*, (1980), (Biochem Biol. Appl. Isotachopheresis), pp. 85–87.

*Primary Examiner*—Richard D. Lovering
*Attorney, Agent, or Firm*—Jacobus C. Rasser; Jack D. Schaeffer; Steven J. Goldstein

[57] ABSTRACT

Calcium 1-hydroxy-3-aminopropane-1,1-diphosphonate forms a gel when mixed with water. As compared to soluble salts of APD, the gel provides slow systemic release and reduced tissue damage when used in the treatment of certain disorders in warm blooded animals.

2 Claims, No Drawings

AQUEOUS GEL CONTAINING TRICALCIUM DI(1-HYDROXY-3-AMINOPROPANE-1,1-DIPHOSPHONATE

TECHNICAL FIELD

This invention relates to diphosphonate gels for use in various therapeutic and cosmetic applications.

Certain diphosphonates, for example, hydroxyethane diphosphonate, amino ethane diphosphonate, dichloromethylene diphosphonate, methylenediphosphonate and 1-hydroxy-3-aminopropane-1,1-diphosphonate are known to be good chelating agents for calcium. Such compounds are therefore useful as e.g., builders in detergent compositions. But a more important utility of these compounds is in pharmaceutical compositions for the treatment of diseases characterized by abnormal calcium metabolism. Another utility is in cosmetic preparations such as toothpaste or mouthwashes for the prevention of dental calculus and plaque deposition.

An important disadvantage of diphosphonates in pharmaceutical applications is that they can cause tissue damage when injected subcutaneously. Another disadvantage is that the level of diphosphonate in the blood reaches a peak within a couple of hours after injection and levels off to less than 10% of the peak value within 5 hours after injection. As a result, many diphosphonates are in significant quantity taken up by the liver or excreted by the kidneys. The benefit/harm ratio of the compounds is therefore not as favorable as one might desire.

It has now been discovered that a specific insoluble calcium salt of 1-hydroxy-3-aminopropane-1,1-diphosphonic acid (hereinafter referred to as $Ca_3(APD)_2$) forms a viscous aqueous gel when stirred with water at a pH of from about 5.5 to about 10. It has further been discovered that this gel has pharmaceutical properties very similar to the soluble sodium salt, but its propensity of causing tissue damage is dramatically less. The systemic release of the gel is slow which results in a lower uptake of APD by the liver as compared to the sodium salt. The slow systemic release provides benefits in a number of therapeutic uses of APD.

It is therefore an object of this invention to provide an aqueous gel of an insoluble calcium salt of APD. It is a further object of this invention to provide pharmaceutical and cosmetic compositions comprising the aqueous gel of the insoluble calcium salt of APD. It is a further object of this invention to provide methods of treatment of calcium disorders virtually without side effects of tissue damage. Finally, this invention provides methods of treatment of calcium disorders which require a slow systemic release of a calcium chelating agent.

BACKGROUND ART

U.S. Pat. No. 3,962,432, issued June 8, 1976, to Schmidt-Dunker discloses pharmaceutical compositions comprising 1-hydroxy-3-aminopropane-1,1-diphosphonic acid (APD) or a soluble salt thereof. The compositions are disclosed to be useful for treating disorders caused by abnormal deposition or dissolution of sparingly soluble calcium salt in the bodies of warm-blooded animals. The insoluble salts of ADP are not disclosed.

P. Gysen and G. Heynen, Anal. Chem. Symp. Ser. (1980) (Biochem Biol. Appl. Isotachoperesis) pp. 85–7, discuss the isotachophoretic determination of the interaction between APD and a fourfold excess of $Ca^{2+}$. At pH 5, 85% of APD was precipitated. Gel formation is not reported.

U.S. Pat. No. 3,608,067, issued Sept. 21, 1971, to Irani, discloses the use of insoluble calcium, magnesium, zinc and aluminum salts of alpha, omega alkylene diphosphonic acids in toothpastes. The insoluble salt particles having a well defined particle size are used as polishing agents having low dentin abrasion values.

SUMMARY OF THE INVENTION

The present invention relates to aqueous gels containing from about 0.01% to about 3% $Ca_3(APD)_2$, hereinafter referred to as "the gel". As compared to soluble salts of APD the gel provides slow systemic release of APD and significantly reduced tissue damage at sites where APD is administered.

In its narrower aspects this invention is directed to pharmaceutical and cosmetic compositions comprising this gel and to improved methods of treating disorders which can normally beneficially be treated with a diphosphonate, which method comprises the step of systemically administering or topically applying the gel to an afflicted human or lower warm blooded animal.

DETAILED DESCRIPTION OF THE INVENTION

By "tricalcium di(1-hydroxy-3-aminopropane-1,1-diphosphonate)" herein is meant the calcium salt of 1-hydroxy-3-aminopropane-1,1-diphosphonic acid which has a molar ratio calcium:diphosphonate of 3:2.

This invention relates to an aqueous gel containing from about 0.01% to about 3%, preferably from about 0.05% to about 1.0%, of $Ca_3(APD)_2$. As compared to the soluble salts of APD and to APD itself, the gel causes dramatically less tissue damage when administered subcutaneously to humans and other warm-blooded animals. Further, the gel is characterized by a slow systemic release as compared to the soluble salts and APD, itself. In spite of this, the gel has the same biological properties as the soluble salts of APD or APD, itself. This unique combination of properties makes the gel extremely useful in a number of pharmaceutical and cosmetic applications of diphosphonates.

The gel is obtained by simple mixing of a solution of a soluble salt of 1-hydroxy-3-aminopropane-1,1-diphosphonic acid with a solution of a soluble salt of calcium. Suitable examples of such soluble salts are monosodium APD and $CaCl_2$. Preferably, the amounts are stoichiometric, (i.e., a Ca:APD ratio of 3:2), or a slight excess of Ca is used. Upon mixing, the pH of the solution is adjusted to a value of from about 5.5 to about 10. A white precipitate is formed. Outside this pH range the stoichiometry of the calcium APD salt is not $Ca_3(APD)_2$, and the salt formed either is soluble, or is insoluble but does not form a gel.

After adjustment of the pH the slurry is allowed to gel. This may take several weeks or more, but when the slurry is stirred a gel is obtained after two or three days.

The gel may also be obtained by dissolving $Ca_3(APD)_2$ at a pH of from about 1 to about 3, and subsequently raising the pH to a value of from about 5.5 to about 10. The slurry obtained upon raising the pH forms a gel after two or three days of stirring.

A freshly prepared gel generally is slightly opaque ("milky"), but becomes clear in the course of two or three weeks.

High concentrations of electrolyte in the slurry negatively affect the gelling properties of $Ca_3(APD)_2$. It may therefore be desirable to subject the slurry to washing with distilled water prior to the gelling step. Washing may be carried out by separating the precipitate with the aid of a centrifuge, discarding the supernatant and resuspending the precipitate in distilled water.

As hereinbefore indicated, the gel of this invention has a dramatically lower propensity of causing damage to soft tissues than prior art diphosphonates. While Applicants do not wish to be bound to a particular theory as to why this is so, apparently, in $Ca_3(APD)_2$, APD's affinity to calcium has been reduced sufficiently to avoid this tissue damage. Yet, the gel has been found to be as effective and to have the same affinity to bone as the soluble salts of APD. This surprising result is believed to be attributable to the unique gel formed by $Ca_3(APD)_2$. For this reason the gel is especially suitable for use in pharmaceutical and cosmetic compositions for oral, topical and systemic administration.

The gel of this invention has also been found to provide slow system release of APD. This significantly alleviates the problem of liver and renal toxicity of this diphosphonate. For example, shortly after subcutaneous dosing of sodium APD solution, there is a high level of the drug in the bloodstream. The body responds by accumulating the drug in the liver and by excreting an important amount of the drug through the kidneys. Upon subcutaneous injection of the calcium APD gel, however, the gel remains at the injection site and is only slow released into the bloodstream. Therefore, the level of drug in the bloodstream is never very high and consequently, the uptake by the liver and excretion by the kidneys is lower than in the case of the soluble sodium APD solution. It has also been found that the gel is useful in intraarticular or subcutanous injection for slow release therapy of adjuvant induced arthritis.

The gel is also useful in other applications that require slow release of diphosphonate compounds like applications to the eye to treat band keratopathy, applications to tooth sockets following extraction, to minimize alveolar bone loss, or packing joints after hip replacement, for preventing calcium accretions on catheters and interuterine devices, for preventing skin and soft tissue calcification, and other treatments in which localized application of a diphosphonate is desired.

Depending on the condition to be treated, the $Ca_3(APD)_2$ gel is either administered systemically or applied topically. Any form of systemic administration is suitable for use herein. It has been found that oral administration of the gel to rats results in a significant deposition of APD on the femur. Oral administration is in many cases preferred over injection and is especially suitable for the treatment of conditions that require only low systemic doses of APD. Examples of conditions which may be treated by systemic administration of a safe and effective amount of the $Ca_3(APD)_2$ gel are arthritis and bone diseases characterized by abnormal bone metabolism. In general, the gel may be used for the treatment of disorders wherein treatment with polyphosphonates is effective. A detailed disclosure of such disorders can be found in U.S. Pat. No. 3,683,080, issued Aug. 8, 1972 to Francis, which disclosure is incorporated herein by reference.

The gel can be administered as is, or mixed with a suitable pharmaceutical carrier. Examples of such carriers are sugars, fatty acids, vegetable oils, glycol, glycerine, and the like. A pharmaceutical composition in unit dosage form contains from about 0.01 mg to about 40 g $Ca_3(APD)_2$, preferably from about 0.1 mg to about 750 mg. Unit dosage forms for oral administration preferably contain from about 10 mg to about 20 g $Ca_3(APD)_2$. Examples of suitable unit dosage forms for diphosphonates are disclosed in U.S. Pat. No. 3,683,080, incorporated herein by reference.

By "safe and effective amount" herein is meant an amount high enough to significantly modify the condition to be treated, but low enough to avoid serious side effects. Due to the slow systemic release the gel is effective at very low dosage rates. Due to the low tissue damaging propensity, rather high dosages can be used without serious adverse side effects. Dosage rates are from about 0.01 mg/kg to about 500 mg/kg, preferably from about 0.05 mg/kg to about 10 mg/kg. Dosages are expressed as mg APD per kg body weight of the patient.

The gel is extremely suitable for various topical applications, either as the gel itself or mixed with other ingredients. Examples are wound pads impregnated with the gel for preventing calcification of wound tissue; mixed with a mint flavor for applications to tooth sockets for minimizing alveolar bone loss, etc. A particularly desirable use of the gel is in a toothpaste. Toothpaste formulations which are suitable for use with the gels of this invention are disclosed in U.S. Pat. No. 3,488,419 incorporated herein by reference. Toothpastes of the present invention comprise from about 2% to about 99% of the gel.

EXAMPLE I

Preparation of the $Ca_3(APD)_2$ Gel 40 ml of a 0.01 M solution of the monosodium salt of APD, pH about 2.5, was mixed with 0.8 ml of a 0.2 M solution of $CaCl_2$. The pH was then slowly raised to 7.4 with KOH. At approximately pH 3 a precipitate began to form. The amount of precipitate increased as the pH was further raised to 7.4. The precipitate was centrifuged, washed three times with about 40 ml of deionized distilled water. After the final wash the precipitate was re-suspended in deionized distilled water to a total volume of 25 ml. This $Ca_3(APD)_2$ slurry was transferred to a 100 ml round bottom flask and stirred. After about three days a firm, milky gel had formed. The gel became entirely clear in the course of about three weeks.

The gel was analyzed for Ca and P. It appeared to contain 0.5% of a salt of APD having the stoichiometry of $Ca_3(APD)_2$.

EXAMPLE II

A precipitate of $Ca_3(APD)_2$ was prepared and washed as described in Example I. The solid was removed from the centrifuge tube and dried. A sample of the dry powder was suspended in deionized distilled water at pH 7.4 and stirred for three weeks. No gel was formed.

Another sample of the dry powder was suspended in deionized distilled water to form a 0.5% slurry. The slurry was acidified with HCl to a pH of 2.5. The precipitate dissolved. Subsequently, the pH was raised with KOH to 7.4. A precipitate was formed, which after about three days of stirring had turned into a gel.

The above experiment was repeated with $Ca_3(APD)_2$ concentrations of 0.05%, 0.1%, 1% and 2%, respectively. In all cases a gel was formed. The 0.05% gel was a viscous liquid. All other gels were firm, their firmness increasing with concentration.

The above experiment was repeated with a 0.5% slurry of the dried powder; after acidification the pH was raised to 10 with KOH. After two days of stirring a gel had formed.

The experiment was again repeated with a 0.5% slurry, but after acidification the pH was raised to only 5. The slurry was stirred for 3 weeks. No gel was formed.

The above method was used in an attempt to form gels from the insoluble salts of APD with barium, magnesium, zinc and strontium. These insoluble salts of APD did not form a gel.

Attempts were made to form gels of the insoluble calcium salt of methylenehydroxydiphosphonate (MHDP), ethylenehydroxydiphosphonate (EPDP), ethyleneaminodiphosphonate (EADP), methylenediphosphonate (MDP) and dichloromethylenediphosphonate ($Cl_2MDP$). None of these salts formed a gel.

Assessment of Tissue Damaging Propensity

Six young male Sprague Dawley derived rats (Harlan) weighing about 250 g were allocated into two groups of three. One group was injected with monosodium APD (0.34 wt.%); 0.2 ml/100 g body weight. The other group with the same amount of APD as $Ca_3(APD)_2$ gel. In a gross postmortem evaluation, examination of the animals injected with sodium APD revealed a large (several cm longest diameter) firm and unmovable enlargement at the site of the injection in the right inguinal area. Ulceration of the skin along the ventral border adjacent to the mass was observed in all animals in this group. Upon dissection, the mass was characterized as firm, pale and roughly spherical. The lesion extended deeply into the tissue but showed no obvious extension beyond the site of injection. The animals treated with $Ca_3(APD)_2$ had much smaller subcutaneous swellings in the inguinal area than those found in animals treated with sodium APD, with no evidence of ulceration on the ventral skin surface. On palpation these masses characteristically were movable and would yield to applied pressure. Upon dissection, lesions from animals in this group were typified as being smaller and extremely well delineated from adjacent normal tissue compared to animals receiving sodium APD. Sodium APD appeared to produce a lesion that is much more extensive grossly than the lesion produced by calcium APD. Also, sodium APD produced ulceration to the skin surface which was not observed with calcium APD. Overall, the soft tissue damage caused by the gel was approximately 1/10 as severe as an equimolar subcutaneous injection of the sodium salt.

Crystal Growth Inhibition Test

The affinity of the calcium APD gel for calcified tissue is demonstrated by the crystal growth inhibition test. This test was developed for polyphosphonates to establish their potential to reduce calcium phosphate deposition and has been shown to be predictive of the affinity of these compounds for calcified tissues like bone. The test is described in detail by Nancollas, et al., Oral Biol. 15, 731 (1970), the disclosures of which are incorporated herein by reference.

In this test, hydroxyapatite seed crystals are added to a calcium/phosphate solution supersaturated with respect to induced precipitation of calcium phosphates but meta-stable toward spontaneous precipitation. The seed crystals induced precipitation and crystal growth. Test chemicals are added to the meta-stable Ca/P solution before seeding. The effect of these chemicals on formation of hydroxyapatite induced by seed crystals has been shown to be indicative of in vivo effects of these chemicals on calcification.

Formation of calcium phosphate crystals results in the release of hydrogen ions (pH change). The rate of crystal growth is monitored by observing the addition of base required to maintain a constant pH. Low levels ($1 \times 10^{-6}$ M) of polyphosphonates are capable of inhibiting the formation of calcium phosphate for 20 minutes or longer. Crystal growth inhibition depends on the propensity of the polyphosphonates to adsorb on calcium phosphate crystal nuclei. The $Ca_3(APD)_2$ gel was compared in this test to the monosodium (soluble) salt of APD. The calcium salt (the gel) was as effective as the sodium salt in inhibiting hydroxyapatite crystal growth.

Biodistribution of the Gel

The calcium and sodium salts of $^{14}C$ labelled 3-amino-1-hydroxypropane-1,1-diphosphonate (14C-APD) were dosed subcutaneously to rats (Sprague Dawley, Charles River) in order to compare distribution and excretion of the two. A dose of approximately 0.5 g of solution or gel containing 2.85 mg APD per ml was injected into the groin area. The animals were sacrificed 72 hours after injection. There were four animals in each group.

TABLE 1

|  | $Ca_3(APD)_2$ Gel % of dose | Na APD Solution % of dose |
| --- | --- | --- |
| Injection site | 66.93 | 26.17 |
| Left femur | .295 | 1.65 |
| Right femur | .298 | 1.69 |
| Liver | .04 | .89 |
| Total Urine | 4.18 | 22.3 |
| Urine |  |  |
| 24 hours | 2.08 | 13.65 |
| 48 hours | 1.11 | 4.67 |
| 72 hours | .98 | 3.98 |
| Total Urine | 4.18 | 22.30 |
| Total Detected | 75.9 | 75.0 |

As can be seen from the foregoing data, the most important difference between the two APD dose forms appears to be the slow release of APD from the calcium salt gel. As a result of this slow release, much less of the diphosphonate is taken up by the liver. Interestingly, the ratio femur/total urine is the same in both cases (0.07) which indicates that the affinity to bone of the calcium APD gel is the same as for the sodium APD solution. Thus, the data indicate that the slower systemic release as results from the insolubility of the calcium salt, reduces the uptake of APD by the liver while allowing normal incorporation into bone.

Adjuvant Induced Arthritis Rat Model

In this animal model, arthritis is induced in rats by injecting them with dead *Mycobacterium butyricum* suspended in mineral oil. The model is described in detail by Francis, et al., Calc.Tiss. Res. 9, 109–21 (1972), The disclosures of which are incorporated herein by reference.

Arthritic animals were treated with a 0.5% gel of $Ca_3(APD)_2$, prepared as described in Example I. Treatment with the gel was started shortly after a severe inflammatory swelling response in the paws of the test animals began. The experimental design is given below.

| Group # | n | Treatment | Route | Freund's Adjuvant |
|---|---|---|---|---|
| 3 | 10 | Ca$_3$(APD)$_2$* | subcutaneous (s.c.) | yes |
| 4 | 10 | Ca$_3$(APD)$_2$* | intraarticular (i.a.) | yes |
| 5 | 10 | saline | subcutaneous | yes |
| 6 | 10 | saline | intraarticular | yes |
| 7 | 10 | none | — | no |

*Calculated systemic dose was 0.06 mg/kg/day as APD. There were 4 doses of 0.1 ml of gel (0.396 mg APD/g) given over 14 days.

Quantitative paw volume measurements were used to determine the inflammatory joint response to the adjuvant injection and to the treatment regimen.

Results

The APD gel significantly reduced the inflammatory joint response to the adjuvant injection whether given intraarticularly in the left paw joint or subcutaneously (in the back)). The intraarticular injections of APD (left paw) did not produce a significantly greater reduction of inflammation in the left paw than the subcutaneous injection. This suggested that there was no significant local effect of the APD. The system effect (right paw swelling reduction) was significant with both i.a. and s.c. injection.

There was a significant but small effect on body weight gain. Animals on APD treatment gained more weight than the saline-treated animals indicating a significant overall systemic benefit to the sick animals.

The results indicate that a very low systemic dose (0.06 mg APD/kg), the calcium APD salt gave a significant systemic benefit, not a local effect, to the arthritic rats. From past data, a dose of disodium ethylene hydroxy diphosphonate of about 0.5–1.0 mg/kg would give a nearly equivalent effect given daily. The gel appears to have a drug reservoir effect.

EXAMPLE III

Capsules are prepared by conventional methods, comprises as follows:

| Ingredient | mg per capsule |
|---|---|
| Ca$_3$(APD)$_2$ gel* | 17,500.00 |
| Starch | 55.60 |
| Sodium lauryl sulfate | 2.90 |

*2% Ca$_3$(APD)$_2$, 98% water

The above capsules administered orally twice daily substantially reduce bone decalcification in a patient, weighing approximately 70 kilograms, afflicted with osteoporosis.

EXAMPLE IV

A toothpaste of the following composition is prepared by conventional methods:

| | Parts by weight |
|---|---|
| Ca$_3$(APD)$_2$ gel* | 33.08 |
| Sorbitol | 6.25 |
| Saccharin | 0.12 |
| Calcium pyrophosphate[1] | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |
| Flavoring | 0.85 |

*2% Ca$_3$(APD)$_2$, 98% water
[1]Prepared in accordance with U.S. Pat. No. 3,112,247 granted November 26, 1963.

This composition effectively retards calculus formation on dental enamel.

What is claimed is:

1. An aqueous gel containing from about 0.01% to about 3% tricalcium di(1-hydroxy-3-aminopropane-1,1-diphosphonate).

2. The gel of claim 1 containing from about 0.05% to about 1% tricalcium di(1-hydroxy-3-aminopropane-1,1-diphosphonate).

* * * * *